(12) United States Patent
Morgan et al.

(10) Patent No.: US 8,591,508 B2
(45) Date of Patent: Nov. 26, 2013

(54) ELECTROSURGICAL PLENUM

(75) Inventors: Roy E. Morgan, Alameda, CA (US);
Wayne K. Auge, II, Santa Fe, NM (US)

(73) Assignee: NuOrtho Surgical, Inc., Fall River, MA (US)

( * ) Notice: Subject to any disclaimer, the term of this patent is extended or adjusted under 35 U.S.C. 154(b) by 334 days.

(21) Appl. No.: 12/580,195

(22) Filed: Oct. 15, 2009

(65) Prior Publication Data

US 2010/0087815 A1    Apr. 8, 2010

Related U.S. Application Data

(60) Continuation-in-part of application No. 12/479,578, filed on Jun. 5, 2009, now Pat. No. 7,819,864, which is a division of application No. 11/847,216, filed on Aug. 29, 2007, now Pat. No. 7,549,989, which is a division of application No. 11/147,481, filed on Jun. 7, 2005, now Pat. No. 7,354,438, which is a division of application No. 10/119,671, filed on Apr. 9, 2002, now Pat. No. 6,902,564, said application No. 11/847,216 is a continuation of application No. 10/486,739, filed on Aug. 24, 2004, now abandoned, which is a continuation of application No. PCT/US02/26277, filed on Aug. 15, 2002, application No. 12/580,195, which is a continuation-in-part of application No. 11/006,079, filed on Dec. 6, 2004, now Pat. No. 7,771,422, which is a continuation-in-part of application No. PCT/US03/18116, filed on Jun. 6, 2003.

(60) Provisional application No. 60/312,965, filed on Aug. 15, 2001, provisional application No. 60/387,775, filed on Jun. 10, 2002, provisional application No. 60/387,114, filed on Jun. 6, 2002.

(51) Int. Cl.
*A61B 18/14* (2006.01)

(52) U.S. Cl.
USPC ............. 606/41; 606/45; 606/48; 606/49; 606/50

(58) Field of Classification Search
USPC ............................. 606/41, 45, 48–50
See application file for complete search history.

(56) References Cited

U.S. PATENT DOCUMENTS 3,903,891 A * 9/1975 Brayshaw ............ 606/27
3,911,107 A   10/1975 Krezanoski
(Continued)

FOREIGN PATENT DOCUMENTS

GB    2037920        7/1980
WO    WO-02/102438   12/2002
(Continued)

OTHER PUBLICATIONS

Chen, S. S. et al., "Heat-Induced Changes in the Mechanics of a Collagenous Tissue: Isothermal, Isotonic Shrinkage", *Transactions of the ASME* vol. 120, 1998, 382-388.

(Continued)

*Primary Examiner* — Lee S Cohen
(74) *Attorney, Agent, or Firm* — Peacock Myers, P.C.; Janeen Vilven; Justin R. Jackson

(57) ABSTRACT

An electrosurgical probe having a plenum which prevents contact of the active electrode with tissue, while simultaneously allowing a fluid/interfacing agents to contact the active electrode.

38 Claims, 10 Drawing Sheets

(56) References Cited

U.S. PATENT DOCUMENTS

| | | | |
|---|---|---|---|
| 3,941,135 | A | 3/1976 | von Sturm et al. |
| 3,982,017 | A | 9/1976 | Thiele |
| 4,014,777 | A | 3/1977 | Brown |
| 4,060,088 | A * | 11/1977 | Morrison et al. ............... 606/49 |
| 4,105,017 | A | 8/1978 | Ryaby et al. |
| 4,266,532 | A | 5/1981 | Ryaby et al. |
| 4,266,533 | A | 5/1981 | Ryaby et al. |
| 4,504,493 | A | 3/1985 | Marshall et al. |
| 4,540,409 | A | 9/1985 | Nystrom et al. |
| 4,615,347 | A | 10/1986 | Schooley |
| 4,872,865 | A | 10/1989 | Bloebaum et al. |
| 4,901,719 | A * | 2/1990 | Trenconsky et al. ............ 606/49 |
| 4,938,970 | A | 7/1990 | Hustead et al. |
| 4,971,068 | A | 11/1990 | Sahi |
| 5,014,699 | A | 5/1991 | Pollack et al. |
| 5,236,456 | A | 8/1993 | O'Leary et al. |
| 5,282,861 | A | 2/1994 | Kaplan |
| 5,304,724 | A | 4/1994 | Newton |
| 5,314,476 | A | 5/1994 | Prewett et al. |
| 5,352,463 | A | 10/1994 | Badylak et al. |
| 5,360,440 | A | 11/1994 | Andersen |
| 5,366,443 | A | 11/1994 | Eggers et al. |
| 5,403,825 | A | 4/1995 | Lagarde et al. |
| 5,458,596 | A | 10/1995 | Lax et al. |
| 5,494,538 | A | 2/1996 | Kirillov et al. |
| 5,498,259 | A | 3/1996 | Mourant et al. |
| 5,514,130 | A | 5/1996 | Baker |
| 5,516,533 | A | 5/1996 | Badylak et al. |
| 5,554,141 | A | 9/1996 | Wendler |
| 5,569,241 | A * | 10/1996 | Edwards ......................... 606/41 |
| 5,569,242 | A | 10/1996 | Lax et al. |
| 5,584,863 | A | 12/1996 | Rauch et al. |
| 5,622,725 | A | 4/1997 | Kross |
| 5,669,904 | A | 9/1997 | Platt et al. |
| 5,669,907 | A | 9/1997 | Platt et al. |
| 5,669,934 | A | 9/1997 | Sawyer |
| 5,683,366 | A | 11/1997 | Eggers et al. |
| 5,697,281 | A | 12/1997 | Eggers et al. |
| 5,697,536 | A | 12/1997 | Eggers et al. |
| 5,697,882 | A | 12/1997 | Eggers et al. |
| 5,697,909 | A | 12/1997 | Eggers et al. |
| 5,741,261 | A | 4/1998 | Moskovitz et al. |
| 5,746,896 | A | 5/1998 | Shimamune et al. |
| 5,749,895 | A | 5/1998 | Sawyer et al. |
| 5,788,976 | A | 8/1998 | Bradford |
| 5,800,385 | A | 9/1998 | Demopulos et al. |
| 5,820,583 | A | 10/1998 | Demopulos et al. |
| 5,824,015 | A | 10/1998 | Sawyer |
| 5,840,166 | A | 11/1998 | Kaneko |
| 5,855,608 | A | 1/1999 | Brekke et al. |
| 5,860,950 | A | 1/1999 | Demopulos et al. |
| 5,871,469 | A | 2/1999 | Eggers et al. |
| 5,885,277 | A * | 3/1999 | Korth ............................. 606/35 |
| 5,885,292 | A | 3/1999 | Moskovitz et al. |
| 5,891,140 | A | 4/1999 | Ginn et al. |
| 5,919,191 | A | 7/1999 | Lennox et al. |
| 5,955,514 | A | 9/1999 | Huang et al. |
| 5,964,968 | A | 10/1999 | Kaneko |
| 6,032,077 | A | 2/2000 | Pomeranz |
| 6,033,654 | A | 3/2000 | Stedronsky et al. |
| 6,086,585 | A | 7/2000 | Hovda et al. |
| 6,112,122 | A | 8/2000 | Schwardt et al. |
| 6,113,596 | A | 9/2000 | Hooven et al. |
| 6,117,109 | A | 9/2000 | Eggers et al. |
| 6,135,998 | A | 10/2000 | Palanker |
| 6,149,620 | A | 11/2000 | Baker et al. |
| 6,159,194 | A | 12/2000 | Eggers et al. |
| 6,162,219 | A | 12/2000 | Nilsson et al. |
| 6,174,309 | B1 | 1/2001 | Wrublewski et al. |
| 6,206,878 | B1 | 3/2001 | Bishop et al. |
| 6,207,134 | B1 | 3/2001 | Fahlvik et al. |
| 6,213,999 | B1 | 4/2001 | Platt et al. |
| 6,214,003 | B1 | 4/2001 | Morgan et al. |
| 6,224,592 | B1 | 5/2001 | Eggers et al. |
| 6,235,024 | B1 | 5/2001 | Tu |
| 6,241,723 | B1 | 6/2001 | Heim et al. |
| 6,241,753 | B1 | 6/2001 | Knowlton |
| 6,264,650 | B1 | 7/2001 | Hovda et al. |
| 6,264,652 | B1 | 7/2001 | Eggers et al. |
| 6,273,883 | B1 | 8/2001 | Furumoto |
| 6,293,942 | B1 | 9/2001 | Goble et al. |
| 6,306,134 | B1 | 10/2001 | Goble et al. |
| 6,309,387 | B1 | 10/2001 | Eggers et al. |
| 6,322,549 | B1 | 11/2001 | Eggers et al. |
| 6,350,276 | B1 | 2/2002 | Knowlton |
| 6,383,184 | B1 | 5/2002 | Sharkey |
| 6,391,025 | B1 | 5/2002 | Weinstein et al. |
| 6,416,509 | B1 | 7/2002 | Goble et al. |
| 6,419,815 | B1 | 7/2002 | Chambers et al. |
| 6,461,352 | B2 | 10/2002 | Morgan et al. |
| 6,463,336 | B1 | 10/2002 | Mawhinney |
| 6,471,993 | B1 | 10/2002 | Shastri et al. |
| 6,547,794 | B2 | 4/2003 | Auge |
| 6,558,382 | B2 | 5/2003 | Jahns et al. |
| 6,743,248 | B2 | 6/2004 | Edwards et al. |
| 6,772,013 | B1 | 8/2004 | Ingle et al. |
| 6,780,178 | B2 | 8/2004 | Palanker et al. |
| 6,824,555 | B1 | 11/2004 | Towler et al. |
| 6,832,995 | B1 | 12/2004 | Towler et al. |
| 6,890,332 | B2 | 5/2005 | Truckai et al. |
| 6,902,564 | B2 | 6/2005 | Morgan et al. |
| 7,004,939 | B2 * | 2/2006 | Mackay ......................... 606/40 |
| 7,066,932 | B1 | 6/2006 | Morgan et al. |
| 7,105,011 | B2 | 9/2006 | Auge |
| 7,354,438 | B2 | 4/2008 | Morgan et al. |
| 7,438,714 | B2 * | 10/2008 | Phan ............................. 606/49 |
| 7,445,619 | B2 | 11/2008 | Auge et al. |
| 7,549,989 | B2 | 6/2009 | Morgan et al. |
| 7,713,269 | B2 | 5/2010 | Auge et al. |
| 7,771,422 | B2 | 8/2010 | Auge et al. |
| 7,819,861 | B2 | 10/2010 | Auge |
| 7,819,864 | B2 | 10/2010 | Morgan et al. |
| 2001/0007940 | A1 | 7/2001 | Tu et al. |
| 2002/0165596 | A1 | 11/2002 | Wilson |
| 2002/0183737 | A1 | 12/2002 | Kristensen |
| 2003/0028189 | A1 | 2/2003 | Woloszko et al. |
| 2003/0036753 | A1 | 2/2003 | Morgan et al. |
| 2003/0216732 | A1 | 11/2003 | Truckai et al. |
| 2003/0216733 | A1 | 11/2003 | McClurken et al. |
| 2004/0082945 | A1 | 4/2004 | Clague et al. |
| 2004/0167244 | A1 | 8/2004 | Auge |
| 2004/0267255 | A1 | 12/2004 | Auge et al. |
| 2005/0085806 | A1 | 4/2005 | Auge et al. |
| 2005/0182449 | A1 | 8/2005 | Auge et al. |
| 2009/0030410 | A1 | 1/2009 | Auge et al. |
| 2009/0306645 | A1 | 12/2009 | Morgan et al. |
| 2010/0069975 | A1 | 3/2010 | Auge |
| 2010/0087815 | A1 | 4/2010 | Morgan et al. |
| 2011/0087308 | A1 | 4/2011 | Morgan et al. |

FOREIGN PATENT DOCUMENTS

| | | |
|---|---|---|
| WO | WO-03/015865 | 2/2003 |
| WO | WO-03103522 | 6/2003 |
| WO | WO-03/103521 | 12/2003 |
| WO | WO-2011047148 | 4/2011 |

OTHER PUBLICATIONS

Fink, Bernd et al., "Holmium: YAG Laser-Induced Aseptic Bone Necroses of the Femoral Condyle", *Arthroscopy: The Journal of Arthroscopic and Related Surgery* vol. 12 No. 12 1996 , 217-223.

Gould, Stephen E. et al., "Cellular Contribution of Bone Graft to Fusion", *Journal of Orthopaedic Research* vol. 18 2000 , 920-927.

Ito, Takayasu et al., "Sensitivity of Osteoinductive Activity of Deminerlization and Defatted Rat Femur to Temperature and Duration of Heating", *Clinical Orthopaedics and Related Research* No. 316 1995 , 267-275.

Janzen, Dennis L. et al., "Osteonecrosis After Contact Neodymium: Yttrium Aluminum Garnet Arthroscopic Laser Meniscectomy", *AJR* 169 1997 , 855-858.

(56) References Cited

OTHER PUBLICATIONS

Lopez, Mandi J. et al., "Effects of Monopolar Radiofrequency Energy on Ovine Joint Capsular Mechanical Properties", *Clinical Orthopaedics and Related Research*, No. 374 2000 , 286-297.

Mourant, Judith R. et al., "Improvements in Laser "Welding" of Chicken Bone Tibias in vitro", *Laser Sciences and Applications Group*, Los Alamos, NM , 1-8.

Mourant, Judith R. et al., "Laser Welding of Bone: Successful in vitro Experiments", *Laser Sciences and Applications Group*, Los Alamos, NM , 1-5.

Rozbruch, S. R. et al., "Osteonecrosis of the Knee Following Arthroscopic Laser Meniscectomy", *Arthroscopy: The Journal of Arthroscopic and Related Surgery* vol. 12 No. 2 1996 , 245-250

Thal, Raymond et al., "Delayed Articular Cartilage Slough: Two Cases Resulting From Holmium: YAG Laser Damage to Normal Articular Cartilage and a Review of the Literature", *Arthroscopy: The Journal of Arthroscopic and Related Surgery* vol. 12 No. 1 1996 , 92-94.

Wall, Michael S. et al., "Thermal Modification of Collagen", *J. Shoulder Elbow Surg.* vol. 8 No. 4 1999, 339-344.

Wallace, Andrew L. et al., "Electrothermal Shrinkage Reduces Laxity but Alters Creep Behavior in a Lapine Ligament Model", *J. Shoulder Elbow Surg.* vol. 10 No. 1 2001, 1-6.

Babincova, Melina et al., ""High-Gradient Magnetic Capture of Ferrofluids: Implications for Drug Targeting and Tumor Embolization"", *Zeitschrift fur Naturforschung*, vol. 56-C, 2001, pp. 909-911.

Brennetor, R et al., "Investigation of Chelate Formation, Intramoecular Energy Transfer and Luminesecence Efficiency and Lifetimes in the Eu-thenoyltrifluoroacetone-triocylphosphine oxide-Triton x-100 System of Using Absorbance, Fluorescence and Photothermal Measurements", *Spectrochim Acta A Mol. Biomol. Spectroscopy, Part A-56*, 2000, pp. 703-715.

Edwards, R B. et al., "Thermometric determination of cartilage matrix temperatures during thermal chondroplasty: comparison of bipolar and monopolar radiofrequency devices", *Arthroscopy* Apr. 2002:18(4), pp. 339-346.

Grant, Kyle M. et al., ""Magnetic Field-Controlled Microfluidic Transport"", *Journal of American Chemical Society (JACS) Article*, vol. 124, No. 3, 2002, pp. 462-467.

Medvecky, Michael J. et al., "Thermal Capsular Shrinkage: Basic Science and Clinical Applications", *Arthroscopy*, 2001, vol. 17, No. 6, Jul. 2001, pp. 624-635.

Minczykowski, Andrzej et al., ""Effects of Magnetic Resonance Imaging on Polymorphonuclear Neutrophil Adhesion"", *Diagnostics and Medical Technology, Medical Science Monitor*, vol. 7(3), 2001, pp. 482-488.

Torchilin, Vladimir P. , ""Drug Targeting"", *European Journal of Pharmaceutical Sciences*, vo. 11, Supplement 2, 2000, pp. S81-S91.

Zhang, Min et al., ""Effects of the Demineralization Process on the Osteoinductivity of Demineralized Bone Matrix"", *J. Periodontaol*, vol. 68 No. 11 Nov. 1997, pp. 1085-1092

Zohar, Ofer et al., ""Thermal Imaging of Reeptor-Activated Heat Production in Single Cells"", *Biophysical Journal*, vol. 74, Jan. 1998, pp. 82-89.

\* cited by examiner

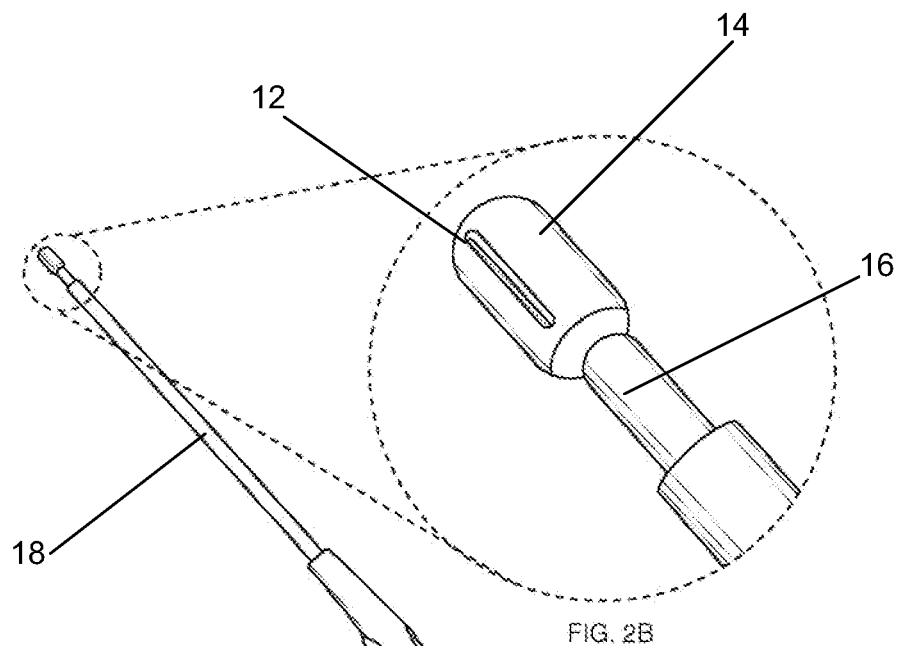
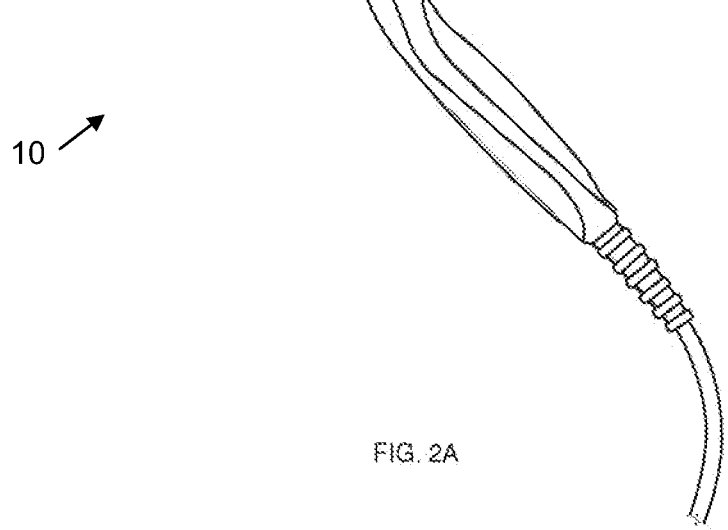
FIG. 2B
FIG. 2A

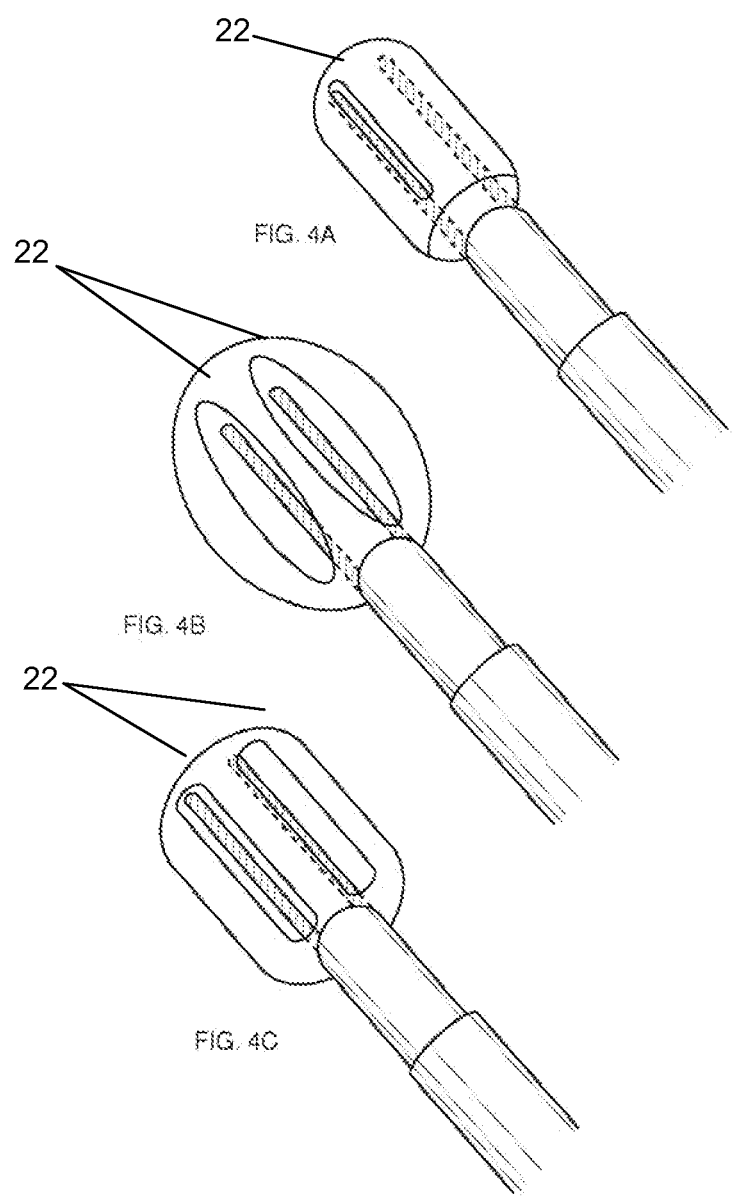

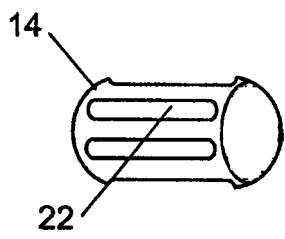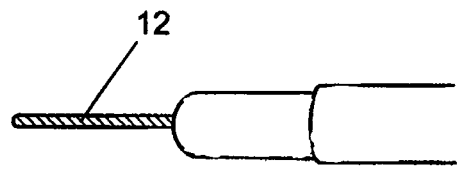
FIG. 7A
(side)
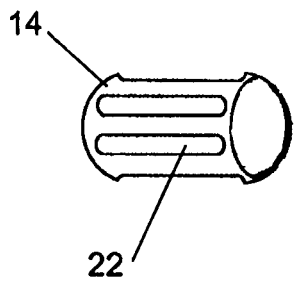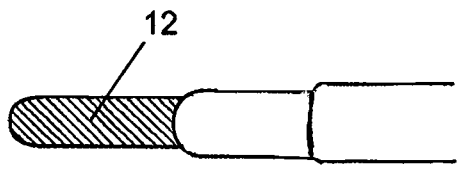
FIG. 7B
(top)

ELECTROSURGICAL PLENUM

CROSS-REFERENCE TO RELATED APPLICATIONS

This application is a continuation-in-part application of U.S. patent application Ser. No. 12/479,578, entitled "Electrosurgery Devices", to Wayne K. Auge, II and Roy E. Morgan, filed on Jun. 5, 2009, issued on Oct. 26, 2010 as U.S. Pat. No. 7,819,864, which itself is a divisional of U.S. patent application Ser. No. 11/847,216, entitled "Electrosurgery Devices", filed on Aug. 29, 2007, and issued on Jun. 23, 2009 as U.S. Pat. No. 7,549,989, which itself is a divisional of U.S. patent application Ser. No. 11/147,481, entitled "Devices for Electrosurgery", filed on Jun. 7, 2005, and issued on Apr. 8, 2008 as U.S. Pat. No. 7,354,438, which itself is a divisional of U.S. patent application Ser. No. 10/119,671, entitled "Methods and Devices for Electrosurgery", filed on Apr. 9, 2002, and issued Jun. 7, 2005 as U.S. Pat. No. 6,902,564, which itself claims priority to U.S. Provisional Patent Application Ser. No. 60/312,965, filed on Sep. 15, 2001, the specifications and claims of which are incorporated herein by reference.

U.S. patent application Ser. No. 11/847,216, entitled "Electrosurgery Devices", filed on Aug. 29, 2007, issued on Jun. 23, 2009, as U.S. Pat. No. 7,549,989 is also a continuation of U.S. patent application Ser. No. 10/486,739, entitled "Methods and Devices for Electrosurgery", filed on Aug. 14, 2004, now abandoned which itself is a continuation of PCT Serial No. US 02/26277, entitled "System and Method of Electrosurgical Biologic Tissue Modification and Treatment", filed on Feb. 13, 2002, which itself claims priority to U.S. Provisional Patent Application Ser. No. 60/312,965, filed on Sep. 15, 2001, and the specifications and claims of which are incorporated herein by reference.

This application is also a continuation-in-part application of U.S. Pat. Application Ser. No. 11/006,079, entitled "Methods and Devices for Electrosurgery", filed Dec. 6, 2004, issued on Aug. 10, 2010 as U.S. Pat. No. 7,771,422, which is a continuation-in-part application of PCT/US03/018116 entitled "Methods and Devices for Electrosurgery", filed on Jun. 6, 2003, which itself claims priority to and the benefit of the filing of U.S. Provisional Patent Application Ser. No. 60/387,775, entitled "Methods and Devices for Electrosurgery and Electrolysis", filed Jun. 10, 2002 and which claims priority to and the benefit of the filing of U.S. Provisional Patent Application Ser. No. 60/387,114, entitled "Methods and Devices for Electrosurgery", filed Jun. 6, 2002, and the specifications and claims (if any) thereof are incorporated herein by reference.

BACKGROUND OF THE INVENTION

Field of the Invention (Technical Field)

Embodiments of the present invention relate to the general field of electrosurgical generators that are used to power devices, such as instrument probes, and instrument probes developed for use in surgical and medical procedures.

The use of electrosurgical instruments in various types of surgical procedures has become widespread and generally consists of a system whereby a treatment device probe is connected to an electrosurgical generator. The device probe delivers the energy from the electrosurgical generator to the tissue treatment site via electrodes to provide a therapeutic effect. Device probe and electrosurgical generator architecture have been developed for particular therapeutic needs, depending upon, for example, the goals of treatment, the tissue type to be treated, and the treatment environment. Most commonly, electrosurgical generators consist of either monopolar or bipolar configurations, or both, which have become well known in the art. Likewise, either monopolar or bipolar treatment device probes have been developed to connect to those types of electrosurgical generators via a dedicated electrosurgical generator output port, either monopolar or bipolar, respectively. Active (or working) and return (reference) electrodes then function in a variety of ways based upon, for example, configuration, architecture, and connection to the electrosurgical generator. In this manner, either a monopolar or bipolar output portal, or both, exists on the electrosurgical generator into which the device probe, either a monopolar or bipolar device respectively, is connected. A monopolar device is connected to a monopolar output portal on the electrosurgical generator and, likewise, a bipolar device is connected to a bipolar output portal on the electrosurgical generator. Typically, feedback from the treatment site is then managed by way of the relevant monopolar or bipolar circuitry within the electrosurgical generator and between the device probe electrodes that are connected to the electrosurgical generator accordingly.

More generally, and to date, the electrosurgical industry has provided a wide variety of products that rely upon the importance of bulk property measurement of in situ structures/components for determining the extent and effect of electrosurgery, which has been well documented. Quantifying energy input indirectly through temperature measurement, fluid field impedance measurement, and fluid field capacitance measurement is believed to effectively correlate the degree to which electrosurgery will effect tissue and the host response thereof. Since such correlations have been extremely inconsistent in practice, a significant amount of confusion has surfaced regarding the validity and accuracy of therapeutic electrosurgical protocols, often leading to the reduction in use of electrosurgical devices for certain applications.

Historical evolution of the prior art has been to provide specific output portals for the most common types of electrosurgery; those being monopolar and bipolar. Each of these output portals is designed to provide specific controls that limit the amount of maximum current, voltage or time-based modulations of current and voltage in response to the variations in factors at the treatment site. The result is intended to control the overall output to the active (working) end of the attached device probe and keep its general state of operation within an arbitrarily selected specified "safe-range" to avoid excessive heat, current, or current density from forming within the surgical site or elsewhere within the patient at the time of treatment. Because of this prior art, the sensing devices at the tip of the probes are limited in their sensing modalities as they relate to these two modes of power output (both Monopolar and bipolar), namely temperature measurement, fluid field impedance measurement, and fluid field capacitance measurement are used to govern power delivery to the probes.

Such circuitry for this monopolar or bipolar configured output portals is contained within the physical confines of the electrosurgical generator enclosure itself, proximal to the connection of the device probe, and is coupled to an electronic and software controller that monitors said variables and continually checks their time-varying values against preset performance limits. When these performance limits are exceeded, the controlling algorithm forces a safety trip, thus modulating or shutting down the primary radio frequency-power output to the working end of the attached device. The specifics of these predefined software controlled trip points is that they are based on the electrophysical constraints electrosurgical generator manufacturers have placed on the output portals, which as previously discussed, are configuration specific (monopolar or bipolar). Thus, the physical spacing of primary components such as the active (working) and return (reference) electrodes plays a paramount role in the variation of those specific characteristics that govern said trip points for safety control.

The overall industry result from this configuration model is a trajectory of "silo" thinking for each specific electrosurgical output portal, meaning that devices have been optimized for either the monopolar output portal or bipolar output portal of electrosurgical generators. Traditional thinking, based on the prior art, has been that there is no advantage in modifying the traditional physical spacing of components typically assigned to any specific output port for any specific mode, meaning that a monopolar procedure that involves a separated ground pad, typically placed at a great distance from the surgical site, has been thought to need such separation to operate effectively. Furthermore, such separation is exactly why the procedure has been named "mono" polar as the electrical poles are separated by such large relative distances that only a single pole is effectively at work within the surgical site. On the other end of the spectrum is the "bi" polar method of electrosurgery which has drawn its name from the physical basis of active (working) and return (reference) electrode proximities to one another. Thus, to date, the industry has remained ensconced in fixed paradigm of one treatment device probe configuration per output port of the electrosurgical generator; i.e. monopolar device to monopolar output port and bipolar device to bipolar output port.

U.S. Pat. Nos. 6,214,003 and 6,461,352, to Morgan, describes a fluid flow through channel that provides the ability for a fluid at the surgical site to flow through both the insulator and the electrode. In that application, the invention provides the flow through channel in the insulator and electrode because the invention seeks to remove things from the active/working electrode so that it can work better in that system. That invention therefore seeks to remove things, like bubbles so that the electrode can re-wet and continue working and effectively without obstruction, thereby enhancing visualization at the surgical site. While that invention may enhance visualization, it does not recognize the advantages of bringing all the elements within the treatment site together so that a reaction therebetween can occur.

U.S. Pat. No. 6,890,332 to Truckai, describes a fixed electrode in a recessed portion of the tip. The tip of that device, however, does not provide protection from the active electrode coming into contact with tissue at a surgical site. This is because the slight recession at the tip does not continue to provide protection from contact with the active electrode when the tip is pushed directly into the tissue. Instead, the tissue merely deforms slightly, thereby allowing the tissue to extend into the slight recession of the tip and thus make contact with the active electrode. Because the impedance value of tissue is different from that of the fluid in the surgical site, each time that the active electrode makes and breaks contact with the tissue, the impedance seen by the electrosurgical generator suddenly changes thereby making it difficult or impossible to adequately regulate the power delivered to the tip of the electrosurgical probe. Furthermore, this is why impedance, capacitance, and even to an extent temperature have been the primary parameters that have been used to control energy output from the electrosurgical generator as described above. This method of regulation of the electrosurgical energy output is extremely inaccurate when placed in a setting where tissue preservation or limited collateral damage is desired because it is often recommended that the user/physician manually induce contact of the active (working) electrode to the tissue in a non-controlled (relative to all users/physicians) manner that then continually alters the impedance, capacitance, sand temperature, the bulk properties, at the treatment site. This leads to a deficit in the ability of the user/physician to effectively control energy deposition and transfer to the treatment site in a method that preserves tissue and prevents collateral damage.

Prior art devices have addressed the problem of continually varying target tissue site impedance through increasingly complex software algorithms that monitor peak voltage outputs from the ESU using rapid circuit sensing and triggering, thereby limiting the output power as the voltage spikes to prevent excessive energy deposition to target tissue sites. These algorithms add significant complexity to ESU monitoring software algorithms and their corresponding validation. Furthermore, in many instances even with rapid peak voltage throttling by software, the total energy output from active electrodes touching tissue remains excessive to prevent significant amounts of necrosis and collateral damage as evidenced by the current literature on the topic.

Additionally, dealing with the large Voltage Standing Wave Ratios (VSWR's) created by these intermittent contacting electrode designs during electrosurgical processes often necessitates use of high-heat bearing signal generating components within the ESU (electrosurgical generator) to provide sufficient stability of the output signal against these reflections. The combined resistive, capacitive, inductive, and reflected impedance can be seen from above as accretive toward the total impedance and thereby produce much greater amounts of heat within the source (ESU). Common examples of such electrical components that must be sized to handle these types of loads include Field Effect Transistors (FET's), Operational amplifiers (Op-Amps), and inductors. The overall size of ESU's is often dictated by the requirements of heat dissipation within the console so as not to yield an excessive external skin temperature on the exterior of the housing.

Thus there is a need for device designs that protect the active (working) electrode from tissue contact and thereby stabilize the primary variables at work in causing fluctuations in load impedance at the surgical site, thus affording ESU designers greater simplicity in construction of hardware/software combinations and in some cases the complete elimination of software, such that "state-machine" electronic logic may be used which is constructed of purely hardware components that can be used to manage the lower VSWR's that are now part of protected electrode operations.

There is thus a need for an electrosurgical probe which houses the active electrode within a protected plenum that prevents contact of the active electrode with tissue, while allowing fluid at the electrosurgical site to make contact with the active electrode, and while simultaneously partially containing gasses created by the electrosurgical process such that they react with one another rather than in a manner that removes the products of electrosurgery away from the treatment site. Additionally, this plenum can then be used as a mechanical implement.

BRIEF SUMMARY OF THE INVENTION

An embodiment of the present invention relates to an electrosurgical tool which has a plenum disposed at least partially around an active electrode, the plenum having one or more openings which permit fluid to enter the plenum chamber, and the plenum shielding tissue from the active electrode. The tool can also have a plurality of active electrodes and/or a plurality of openings in the plenum. An exterior surface of the plenum can be textured, which texture can be a roughened surface. Optionally, the plenum can have a shape useful for a surgical procedure, which can include a knife blade, which knife blade can optionally be serrated. In one embodiment, the openings can be on an end-portion of the plenum. The plenum can have at least one elongated opening orientated along its primary axis, or a plurality of elongated openings orientated along its primary axis. In one embodiment, the active electrode itself does not have any openings, flow-through channels, portals, and/or windows.

An embodiment of the present invention also relates to a method for performing an electrosurgical procedure which includes providing an electrosurgical apparatus having active and return electrodes; and disposing a plenum around the active electrode, the plenum comprising one or more openings which permit entry of fluid while preventing anatomically-specific tissue structures from contacting the active electrode. The anatomically-specific tissue can be targeted tissue and/or in-tact tissue. Optionally, the openings of the plenum can be disposed along a primary axis of the plenum. In the method, at least a portion of the plenum can extend beyond at least a tip of the active electrode. In one embodiment, the plenum does not comprise merely a recessed electrode.

An embodiment of the present invention relates to an electrosurgical tool having a plenum disposed at least partially around an active electrode, the plenum having a plurality of openings which permit fluid to enter the plenum chamber. The openings in the plenum can be small enough to inhibit and/or prevent the ability of intact tissue from entering the plenum.

An embodiment of the present invention also relates to an electrosurgical tool having a plenum disposed at least partially around an active electrode, the plenum having one or more openings which permit fluid to enter the plenum chamber, the openings being less than about 100% of any side of the plenum. Optionally, the openings can be less than about 80%, 70% 50%, or 35% of any side of the plenum.

An embodiment of the present invention also relates to an electrosurgical tool having a plenum disposed at least partially around an active electrode, the plenum having one or more openings which permit fluid to enter a chamber of the plenum, the plenum not entirely open on a tip thereof. The openings can be small enough to inhibit the ability of intact tissue from entering the plenum. The openings can be small enough to prevent intact tissue from entering the plenum.

An embodiment of the present invention also relates to an electrosurgical tool having an electrode surrounded on all sides by a plenum surface, the plenum surface having one or more openings which provide fluid flow and communication of a fluid past the active electrode. In one embodiment, the shape, size, and/or location of the one or more openings can be selected such that the fluid travels past the active electrode at a predetermined velocity.

Aspects, advantages and novel features, and further scope of applicability of embodiments of the present invention will be set forth in part in the detailed description to follow, taken in conjunction with the accompanying drawings, and in part will become apparent to those aspects and advantages of embodiments of the present invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIGS. 2A and B are drawings which illustrate an embodiment of the present invention whereby the electrosurgical device has a plenum disposed on its tip which prevents the active electrode from contacting tissue during an electrosurgical procedure and allows all the elements of electrosurgery to inter mingle or be brought to the active (working) electrode;

FIGS. 4A-C are drawings which illustrate alternative plenum configurations according to an embodiment of the present invention;

FIGS. 7A and B are partially exploded view drawings which illustrate a plenum that can be placed about a single active electrode which single active electrode can respectively be thin or thick;

DETAILED DESCRIPTION OF THE INVENTION

In one embodiment, the present invention allows the general field of electrosurgery to use electrosurgical generators to power devices, such as instrument probes, developed for use in surgical and medical procedures.

As used throughout the specification and claims of this application, the term "plenum" is given a broad meaning and is intended to mean any type of a cage, guard, protective structure, or other device, system, method, apparatus, capable of at least partially housing an active electrode and inhibiting the ability for the active electrode to come into contact with a portion of tissue which is outside of the plenum. The term "plenum" also includes a device, method or apparatus that regulates the media and products by providing a mechanism for mechanically restricting the inflow of fluid and the outflow of the endogenously produced gases during electrosurgery at or about the active (working) electrode(s). The term "plenum" does not mean a mere slightly concave structure which permits tissue to come into contact with the active electrode when the tissue is pressed against the plenum.

Figure 1:
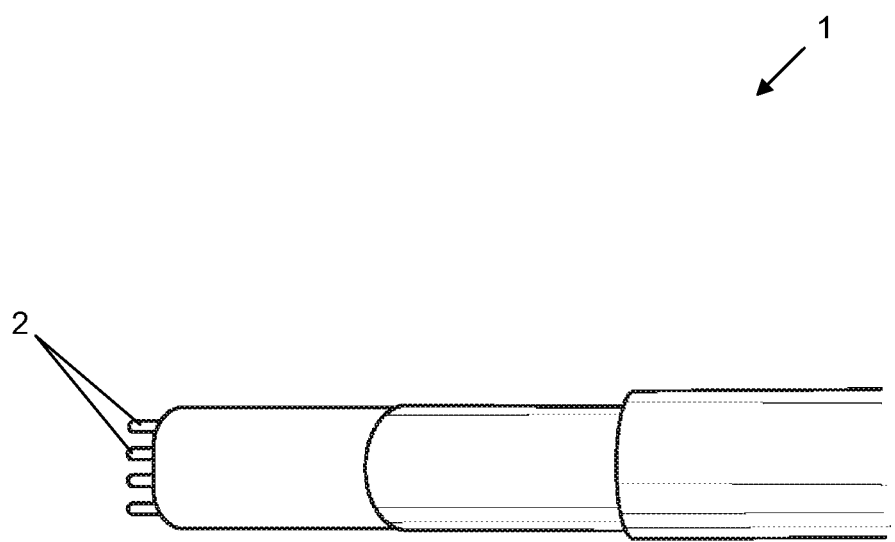
FIG. 1 is a drawing which illustrates the prior art traditional method of delivering high frequency electrical current to the human body during a treatment procedure.

As illustrated in FIG. 1 prior art electrosurgical devices 1 typically comprise one or more exposed active electrodes 2 which project from an end thereof. In typical electrosurgical applications, the surgical site is submerged in a conductive saline solution. The high frequency electric current flowing through the active electrodes and into the patient thus encounters differing amounts of impedance dependent upon whether the probe is contacting tissue of the patient or only the interfacing media. Accordingly, differing amounts of power are provided to the surgical site as the active electrodes 2 come in and out of contact with tissue of the patient.

As illustrated in FIGS. 2A, and B, the present invention comprises electrosurgical probe 10 having active electrode 12 housed within insulating plenum 14. Desirable results can be obtained when probe 10 is operated in a monopolar mode or a bipolar mode. When operated in a bi-polar mode, return electrode 16 is optionally disposed slightly proximal along lumen 18 from insulating plenum 14. In an alternative embodiment, an active and reference electrodes can optionally be disposed within insulating plenum 14. In yet another embodiment active electrode 12 can be housed within plenum 14 and plenum 14 can optionally be formed from a conductive material and used as a return electrode or as a portion of the return electrode.

In a preferred embodiment, insulating plenum 14 is made from a non-conductive material which most preferably comprises a glass, ceramic, or other material which can withstand high electric voltage and high temperatures whereby the plenum is a mechanical implement used to assist or for treatment.

Figure 3A:
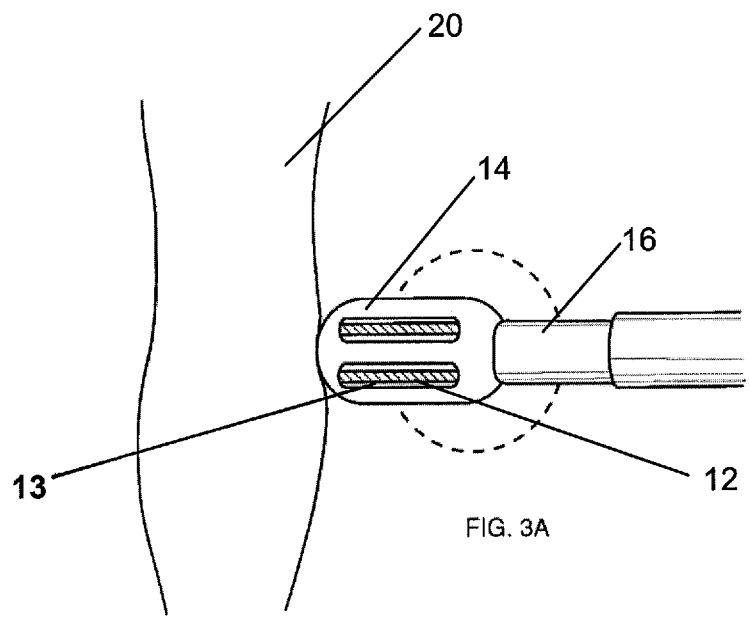
FIGS. 3A and 3B are drawings which respectively illustrate an embodiment of the present invention and a prior art device pressed against tissue and the theoretical current flow lines from the active electrodes to the return electrodes therefrom.
Figure 3B:
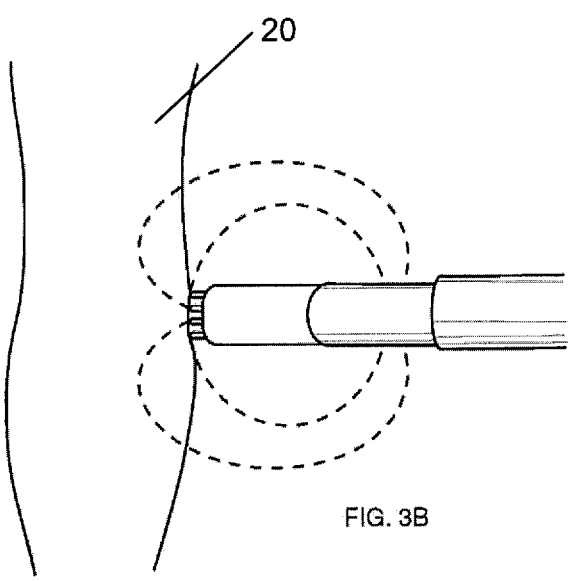

As illustrated in FIGS. 3A and 3B, which respectively illustrate the probe of the present invention and a prior art probe each contacting tissue 20 at a surgical site. The dashed lines illustrate current flow paths from the active electrodes to the return electrode. As can be seen in the drawing, the current flow paths, and thus impedance, is much more constant and predictable with the probe of the present invention since only the fluid at the surgical site acts as the conductor between the active and return electrodes, whereas the tissue also acts to conduct the flow of electricity with the prior art device, particularly when the active electrode is in contact therewith. Not only does the present invention thus permit a more constant and predictable amount of power to be delivered to a surgical site, and thus more predictable surgical results, but the present invention also greatly reduces the potential for significant current flow through the tissue, such current flow can cause damage to the tissue, thus making the present invention a safer surgical tool than the devices of the prior art. Furthermore, the shape of the electrode can then be optimized for its electrical properties rather than for tissue interfacing properties which all prior art exemplifies. For example, a sharpened edge of the active (working) electrode provides for beneficial electrical properties in a conductive or electrolyzable environment by optimizing current density at the solid (electrode)/fluid (interfacing media) contact points as opposed to within the tissue as all prior art exemplifies.

Figure 5:
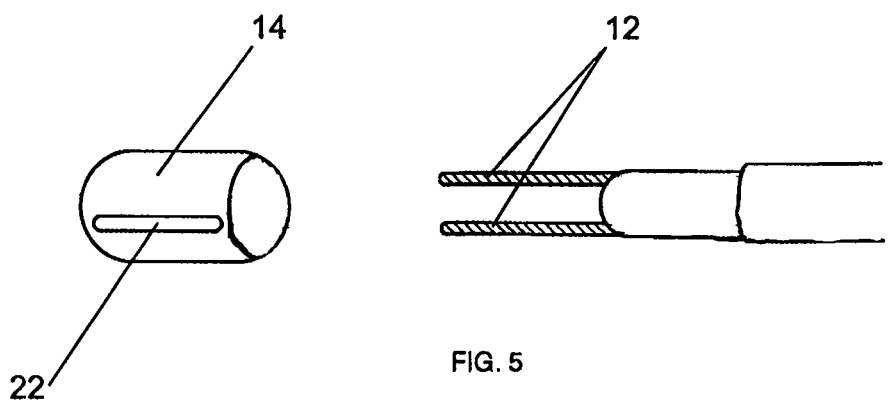
FIG. 5 is a partially exploded view drawing which illustrates a plenum that can be placed about a plurality of active electrodes.
Figure 6A:
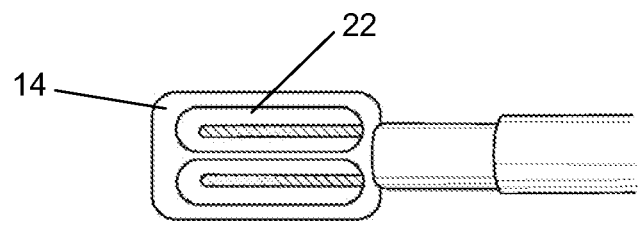
FIGS. 6A-D illustrate different configurations of a plenum according to an embodiment of the present invention.
Figure 6B:
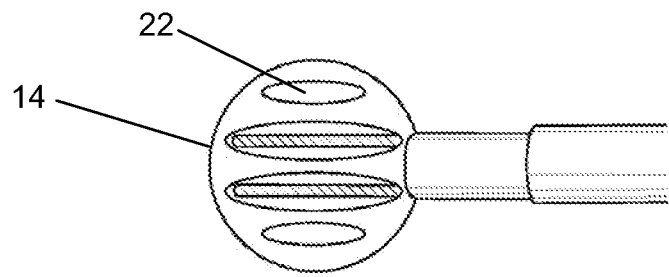
Figure 6C:
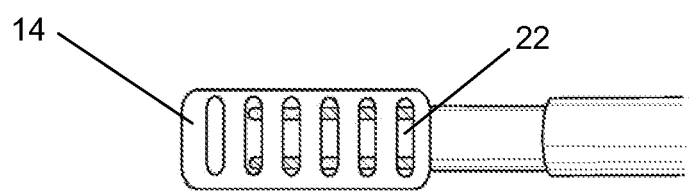
Figure 6D:
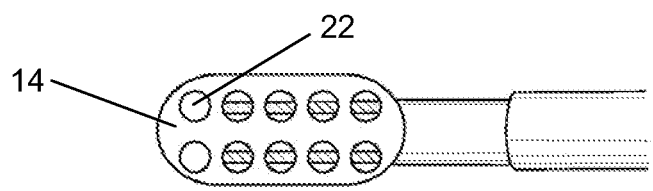

Referring now to FIGS. 4A-5, in one embodiment, a plurality of active electrodes 12 can optionally be disposed within plenum 14. One or more openings 22 are preferably provided in plenum 14 such that fluid at the surgical site can enter and exit the plenum chamber (i.e. the inner area of plenum 12), while tissue is excluded from the inner area of plenum 12. FIG. 5 illustrates a partially exploded view such that the plurality of active electrodes 12 are exposed.

FIGS. 6A-D illustrate a few of the possible configurations of plenum 14 and openings 22. Neither the particular shape of plenum 14 nor the shape, size, location or number of openings 22 are essential to the present invention. Upon studying this application, those skilled in the art will readily appreciate that desirable results can be obtained from multiple shapes, types and sizes of plenum 14 and openings 22. Furthermore, the plenum can be used as a mechanical implement that aids the user/physician during treatment.

FIGS. 7A and 7B respectively illustrate partially exploded side and top views of an embodiment of the present invention wherein a single active electrode 12 is provided, which active electrode comprises a thin and wide shape.

Figure 8A:
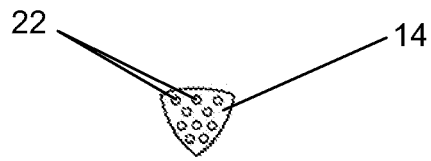
FIGS. 8A and B are side and end view drawings which illustrate an embodiment of the present invention wherein the plenum comprises a knife blade with a plurality of openings disposed on an end thereof.
Figure 8B:
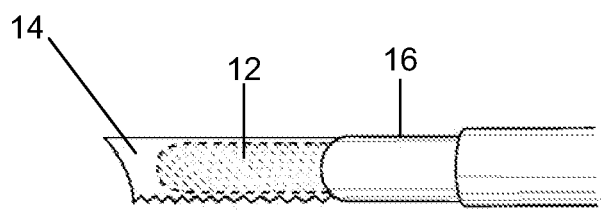
Figure 9:
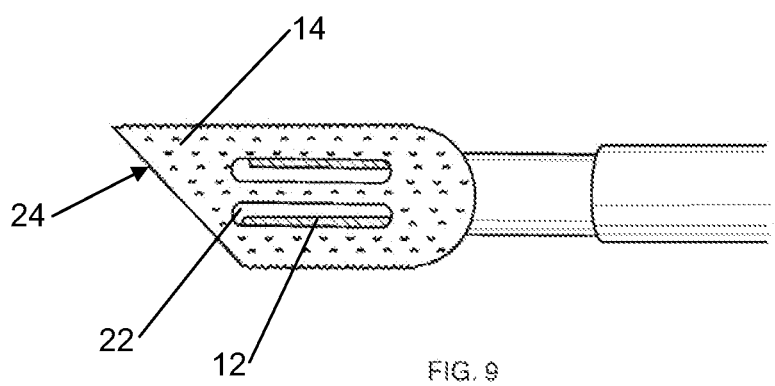
FIG. 9 is a side-view drawing which illustrates an embodiment of the present invention wherein the plenum comprises a knife end, a plurality of side openings; and roughened surface.

FIGS. 8A and 8B are drawings which respectively illustrate end and side views of an embodiment of the present invention. As can be seen, plenum 14 can have a shape, texture, and/or design which provide additional benefits during a surgical procedure. As illustrated in those FIGS., plenum 14 comprises a knife-blade shape which permits a surgeon to simultaneously make physical cuts during an electrosurgical procedure. A knife-blade shape, which can be serrated, is particularly effective if the plenum is made from a hard material, such as a ceramic. In this embodiment, openings 22 are placed at the tip of plenum 14, however one or more holes can optionally be disposed in a different location. Other shapes and textures of plenum 14 can also be desirable. FIG. 9 illustrates but one such shape and texture. As illustrated therein, plenum 14 preferably comprises a textured or roughened surface, for example a rasp-type surface, which can be useful for filing and/or grinding during an electrosurgical procedure. In addition to a textured surface, plenum 14 can also optionally comprise an additional useful shape, such as blade 24. The plenum can serve as a stabilizing platform for the device against the tissue surface. This provides tactile feedback to the user/physician during treatment. Accordingly, any useful configuration can be created by those skilled in the art, such as but not limited to ball tip, flat tip, needle tip, rubber tip (as in a composite plenum), curette tip, mellonbailer tip, potato-peeler like tip, and the like. Composite material plenums are particularly useful to add an additional feature for the user to gain information from the treatment site at the tip of the probe.

FIG. 3A illustrates just such a composite plenum wherein an elastomeric lip 13 is disposed along the edge of Plenum 14 opening 22. Elastomeric lip 13 provides the ability to engender variable force tactile feedback to the user as compression is made up against tissue surfaces. The location of and dimensions of such elastomeric composite features are not limited to the specifics shown in FIG. 10B, but are representative of a composite feature set of the plenum entry or plenum exterior that enhance tactile feedback intraoperatively to the user. Such composite system combinations of semi-rigid elastomers and rigid insulating materials form a basis for a translating electrode/plenum assembly that is controlled by the force with which the user applies to compress it against the target tissue site.

Figure 10A:
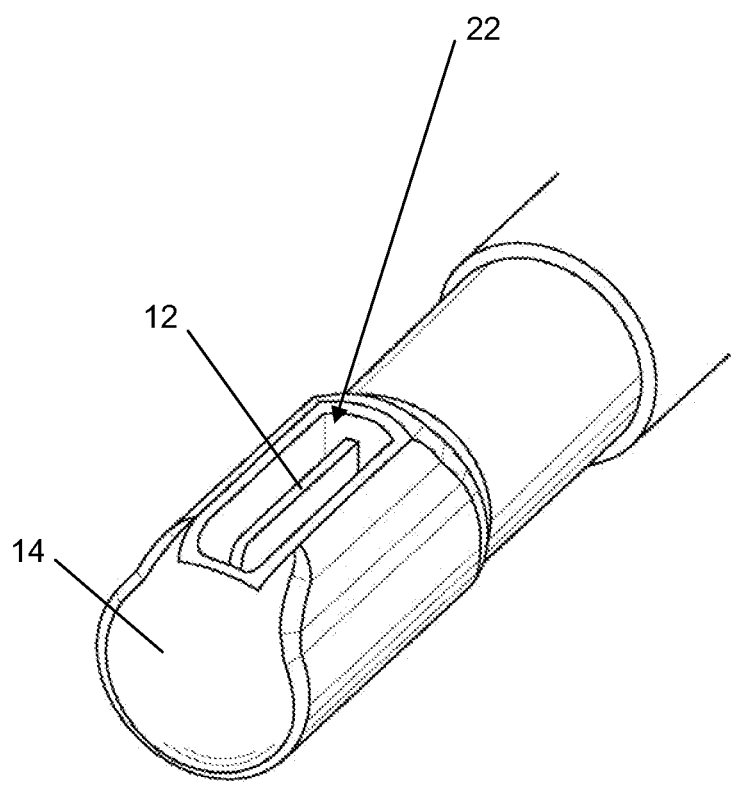
FIGS. 10A and 10B illustrate embodiments of the present invention wherein the plenum is respectively dull and sharp around the opening therein.
Figure 10B:
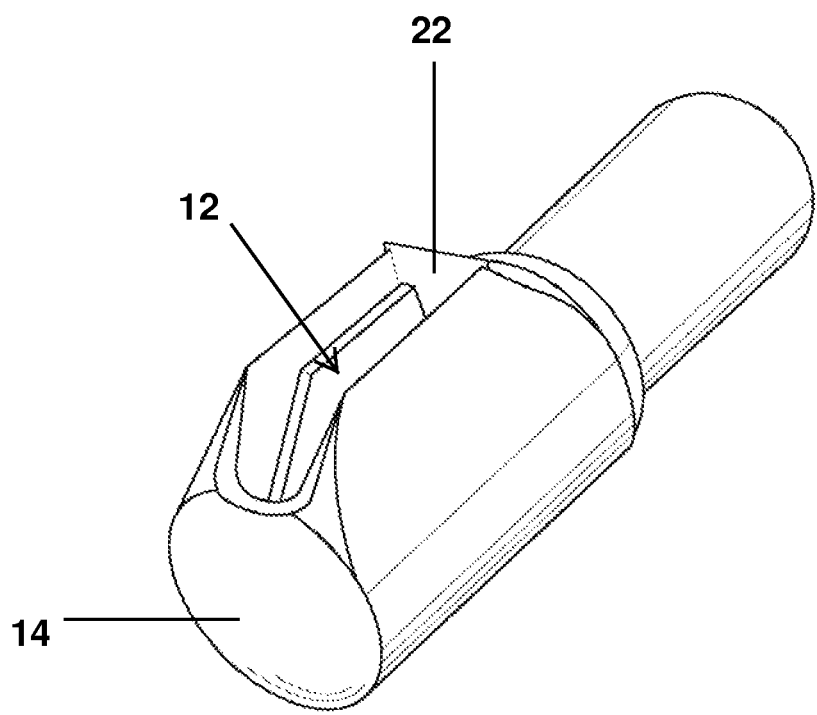

FIG. 10A illustrates an embodiment wherein the portions of plenum 14 surrounding opening 22 are dull. F*igure* 10B illustrates an embodiment of the present invention wherein plenum 14 is sharp around opening 22 thereby providing a surgeon with a physical cutting apparatus while simultaneously providing an electrosurgical apparatus.

In one embodiment, the opening in the plenum is preferably dimensioned for specific procedures to protect tissue of the most common anatomical dimension expected to be encountered in the specific procedure from entering the plenum.

Embodiments of the present invention preferably provide the reduction and/or elimination of excessive field-effect transistor, OP-Amp, and/or inductor usage in the construction of primary radio frequency ("RF") delivery circuitry within electrosurgical console unit ("ESU"). The outcome of voltage standing wave ratio stabilization is less heat production within the ESU and the reduction in size of the ESU. Where probe designs hold total impedance to 100Ω or less, console sizes can preferably be reduced by as much as 50%-75% in size. This provides a mechanism by which ESU's can be designed to fit ever-increasing limits in space and space competition within the operating room for consoles specific to various procedures. Further, as the size decreases, it may be housed within the hand piece of the device itself make the electrosurgical probe cordless, with a self-contained power source and circuitry.

More specifically, in one embodiment, the present invention relates to specific methods of connection of such devices to electrosurgical generators that provide active enhancement of output signal monitoring. Embodiments of the present invention also relate to specific management of circuit characterization when a single mode output from an electrosurgical generator is bridged to perform a circuit contraction in physical space. Embodiments of the present invention also preferably provide improved system level reliability as there is a significant reduction in the system's dependency upon software for maximum output power governance and emergency shut-down. In some embodiments, the present invention can be used in real-time electrophoresis or drug-infusion (patch) technology (battery powered drug patches that accelerate drug infusion).

With the present invention, a significant reduction in the size of the ESU enclosure is achieved through the reduction of output power governance controls to "state-machine" or simplified software control, both of which reduce the necessary RAM, watch-dog, and Front-Side-Bus speed, requirements of the ESU. All of these reductions in component capacities translate to less circuit board-space being required as parts of equivalent capacity are smaller and require less power to drive at the circuit-board level.

When using RF generators like the Force 2 (ValleyLab), there are four things that stand out and may affect performance from one model of generator to another brand or model (especially newer models), these include:

1. There is no absolute definition of COAG or CUT functions. The waveform (time on/off) and waveshape (being a sinusoid or something else) will vary from model to model.

2. Most generator models have a few types of COAG and these will affect performance and will be available for the user to select. In cases where specific models may have very high COAG output voltages (6,000V-9,000V), reliability/durability questions of device electrical integrity are often raised.

3. The power curve (the power output relative to the electrical impedance seen at the device) of the particular model will have a direct impact on performance. Many older generators have a triangular shaped power curve, such that the power value on the display is only true at a certain impedance. Operating at an impedance larger or smaller than the "ideal" impedance will result in less output power than displayed on the ESU.

4. Newer generators have software controlled power output such that the power curve changes from a triangluar shape with a single peak to a trapezoidal shape plateau which is mostly the same output as impedance raises or lowers. These dynamic responses force clinicians to adjust their technique in a concomitant way depending on which device/system pair they are confronted with at the time of any given surgery. Therefore, the power settings are regularly altered, which will again affect performance and may require a lower set power to achieve desired clinical effects when equipment platforms are varied. This is additionally confounded by the change in impedance, capacitance, and temperature at the treatment site by the contact of the active (working) electrode to the tissue that is necessary with prior art devices.

Embodiments of the present invention directly addresses the first three performance variables through reduction of the intrinsic impedance of the overall procedure; by eliminating tissue contact with the active electrode. In the fourth instance the same architectural approach mates well with fast-acting software control to provide yet smoother responses to the ESU that yield stable and predictable electrode operations to the user.

Embodiments of the present invention address three specific categories of features for the design of a plenum chamber in accordance with the present invention:

1. Mechanical. Mechanical features of the plenum housing which provide additional useful surgical features, i.e. sharp, rasp, cutter, potato-peeler like blade, mellon-bailer like scoop, tactile feedback, and general protection of the tissue from the active/working electrode.

2. Fluid Flow. The plenum controls the fluid flow and hence the treatment site reactions. It also allows for the fluid flow to buffer and/or protect the tissue in a cooling manner to avoid the application of excessive heat to the treatment site. The fluid or media can be configured more specifically, like fluids, gels, semi solids and the like that are either conductive or electrolyzable.

3. Electrical. Since the present invention provides the ability for the active/working electrode to operate without touching the tissue, impedance changes far less than in other prior art devices because the tissue, which is the prime driver of impedance change during treatment, is not involved. Impedance fluctuations are buffered so as to better control energy deposition at the treatment site. The present invention also, allows different configurations of the power source, and makes the stability of power deposition at the treatment site safer. Sensing devices are also able to be more effectively used since impedance is no longer necessarily the prime measurement that is used for feedback control. This permits numerous sensors to optionally be used, including but not limited to temperature sensors and pH sensors as more fully described in U.S. patent application Ser. No. 11/006,079.

The general form of the function for impedance of the arthroscopic electrosurgical circuit in-vivo can be approximated by the following generalized function:

$$Z_{TOT} = f[(Z_{tissue} + Z_{media} + Z_{probe}), x, t]$$

If the objective is to understand time-variation of this function it follows that:

$$\frac{\partial Z_{TOT}}{\partial t} = \frac{\partial z_{tissue}}{\partial t} + \frac{\partial z_{media}}{\partial t} + \frac{\partial z_{probe}}{\partial t} + \frac{\partial x}{\partial t} + 0$$

However, in traditional contact electrosurgery, the limits of distance of probe to target tissue site are known to approach zero (i.e. the electrode must contact the tissue):

$$\lim_{x \to 0} \frac{\partial Z_{TOT}}{\partial t} = \frac{\partial z_{tissue}}{\partial t} + \frac{\partial z_{media}}{\partial t} + \frac{\partial z_{probe}}{\partial t} + 0;$$

Additionally, it is important to note that the internal probe impedance with respect to time is effectively a constant:

$$\not{c} \quad \frac{\partial z_{probe}}{\partial t}$$

This is because the conductors within the probe consist of stable elements of copper wire conductors whose metallic conductance values (material resistivities) vary little, and therefore do not significantly contribute to the time based variation of impedance.

What remains as the dominant elements of impedance time-based variation is:

$$\lim_{x \to 0} \frac{\partial Z_{TOT}}{\partial t} = \frac{\partial z_{tissue}}{\partial t} + \frac{\partial z_{media}}{\partial t} + \phi \quad \text{(Eq.-1)}$$

Of these elements, the known values for media conductivity (NaCl, 0.09% by weight) are relatively constant even given a relatively small amount of thermal variation in bulk fluid properties (Resistivity typically in the range of 80-110 $\Omega$-cm). This can be restated as: 95$\Omega$-cm±15 $\Omega$-cm; illustrating that the relative magnitude of impedance shift (variance) within the media alone represents approximately a 16% variation.

Next, reviewing known parameters of tissue induced impedance in the electrosurgical circuit when in direct contact with probe active electrodes; many electrosurgical manuals indicate that load impedances typically exceed 500$\Omega$ into a variety of tissue types. Even under the assumption of equivalent variation (16% of nominal, 500$\Omega$) the total impedance change is equal to 79$\Omega$. This represents a five-fold (5×) increase in overall impedance from that of the interfacing media alone. If we use this nominal approach we can rewrite Eq.-1, above as:

$$\lim_{x \to 0} \frac{\partial Z_{TOT}}{\partial t} = 5\left[\frac{\partial z_{media}}{\partial}\right] + \frac{\partial z_{media}}{\partial} + \phi; \quad \text{(Eq.-2)}$$

What this reveals is that during application of RF energy to tissue in domains below plasma, tissue impedance is the dominant factor by at least half an order of magnitude. It is worthy of note, that typical impedance variations have been noted in the laboratory that exceed 30% in tissue contacting electrosurgery which amplifies the stark magnitude difference in Eq.-2 to an even larger extent.

It should now be straightforward to understand that RF electrosurgery, when controlled below plasma levels, provides a more stable impedance environment and enables a more predictable output response of probe technology in relation to applied power. When the benefits of protected electrodes are introduced in below plasma controlled RF electrosurgery Eq.-2 is now dominated only by media impedance variations and is rewritten as follows:

$$\lim_{x \to 0} \frac{\partial Z_{TOT}}{\partial t} = \frac{\partial z_{media}}{\partial t} + \phi$$

But this was already identified as being 95 $\Omega$-cm±15 $\Omega$-cm, previously. Thus, RF signal/power generator feedback fluctuations for protected electrodes no longer have to deal with rapid and significant swings in Voltage Standing Wave Ratios (VSWRs) and the need for rapid response software control of current flow and voltage output is minimized. FIGS. 1 and 2, below illustrate the differences practically between the Prior-Art and the new State-of-the-Art introduced by NSI.

Embodiments of the present invention provide a protected electrode geometry combined with the reductions in dynamic impedance change that is inherently part of a protected electrode architecture. These embodiments thus provide a more stable platform of low-energy RF electrosurgery below plasma domains. As such, clinicians can benefit from the many and varied applications of RF energy on various tissue types that provide for more complete healing response and lower energy deposition to target tissue sites. These provide the benefit of less harm to healthy tissue and a more complete participation of surrounding tissue, which unharmed by virtue of this architecture, in the overall healing response.

Embodiments of the present invention provide a reduction or elimination of the mismatched impedance of a load in an electrosurgical circuit created by variations that are naturally occurring when tissue contacting electrodes are utilized. Traditional electrosurgery has involved the direct contact of active electrode elements with human tissue where the end result has been to cut, dissect, or ablate the tissue structure. Since the characteristic impedance of such tissue structures is primarily defined by their relative water/electrolyte content (NaCl) as the typical procedure progresses with an electrode in direct contact with tissue, there is a desiccating function that naturally reduces this electrolyte content and thus raises the characteristic impedance during sustained application of RF energy to a target tissue site. This process also induces metabolic effects that the host tissue needs to accommodate.

Typically electrical feedback circuitry built into electrosurgical units (ESUs) are designed to detect high-impedance reflections causing Voltage Standing Wave Ratio's (VSWR) within the primary RF output circuit, defined as:

$$VSWR = \frac{(1 + \Gamma)}{1 - \Gamma},$$

where:

$$\Gamma = \frac{(Z_L - Z_O)}{(Z_L + Z_O)}$$

Note that the source impedance $Z_O$, is essentially that defined by the ESU, connector, cable and the Probe. The Load impedance $Z_L$, is the impedance of the interfacing media, tissue, and return electrode. What becomes evident to those skilled in the art, is the time-varying nature of the impedance and its functionally dependant variables. The raw interfacing media, most commonly NaCl (0.5%-0.9% by weight) has a nominal impedance of 55$\Omega$-100$\Omega$ depending on a host of variables that include:

a. Tissue type being contacted (water/electrolyte content)
b. Temperature of the interfacing media
c. Distance of the active electrode to tissue structures
d. Bulk velocity of the fluid field immediately about the active electrode
e. Exposed surface area of the active electrode
f. Distance between the active and return electrodes
g. Random field effects of physio-chemical actions including electrolysis Embodiments of the present invention provide protected electrode probe configurations thus eliminating the variations caused by (a) and drastically limit those caused by (b) above.

As contact with tissue is by design prevented, the total impedance variations with time are drastically reduced that could result from tissue desiccation. Current pathways are provided for in the electrode design that can traverse adjacent to tissue from the active electrode to the return electrode through the interfacing media only without affectation by the tissue or its relative conductivity as determined by its state of hydration. This technique as disclosed herein allows for a more specific involvement of the interfacing fluid/media by which the energy of the electrosurgical generator is transferred or deposited at the treatment site. The work of this energy is on the interfacing media primarily, and avoids the higher current densities within tissue of the prior art. These interfacing media interaction are those that would occur within a conductive or electrolyzable media.

When one considers the remaining variables it is clear that (b) and (d) are strongly related as the bulk velocity increases, the temperature will approach the constant of the bulk bag temperature of the saline fluid being infused. Note also that (e) and (f) are fixed quantities based on the specific design of the probe under evaluation. Also note that the protected electrode design limits the minimum distance that the active electrode can be brought toward tissue. The net result is that of the variables at play, in a protected electrode probe design, only (g) remains as a major player in control variables.

For energy levels in the COAG domain (0-180 Watts output power), (g) is nearly linear and increases with output power. This stabilization of large variations in impedance through elimination and reduction of component impedance functions within the electrosurgical environment result in lower VSWR's in the transmission lines of the ESU and Probe. When such conditions are minimized an output circuit is said to be "matched" to its impedance load. While these conditions will not be exact due to the technique dependent factors at play intra-operatively, they are significantly reduced, creating a safer device.

In one embodiment, a preferable distance is from about 0.5 mm to about 5 mm. More preferably, distances of active electrode protection range from about 0.5 mm to about 2 mm.

Although the description above contains many specific examples, these should not be construed as limiting the scope of the invention but merely providing illustrations of some of the presently preferred embodiments of this invention. Thus, the scope of the invention should be determined by the appended claims and their legal equivalents, rather than narrowed by the specific illustrative examples given.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An electrosurgical tool comprising:
   a lumen;
   an at least rigid plenum formed from a non-conductive material and disposed on a distal end of said lumen, said plenum disposed at least partially around a first electrode, said plenum comprising a plurality of openings and said plenum shielding tissue from said first electrode; and
   said first electrode coaxial with a second electrode.

2. The tool of claim 1 wherein said first electrode comprises a plurality of electrodes.

3. The tool of claim 1 wherein said plenum exterior comprises a textured surface.

4. The tool of claim 3 wherein said textured surface comprises a roughened surface.

5. The tool of claim 1 wherein said plenum comprises a shape useful for a surgical procedure.

6. The tool of claim 5 wherein said plenum comprises a knife blade.

7. The tool of claim 6 wherein said knife-blade is serrated.

8. The tool of claim 1 wherein said lumen comprises said second electrode.

9. The tool of claim 1 wherein said first electrode does not comprise any openings or flow-through channels.

10. A method for performing an electrosurgical procedure comprising:
    performing an electrosurgical procedure by contacting first and second electrodes with an aqueous fluid at an area to be treated, wherein the first and second electrodes are coaxially arranged and wherein an at least rigid non-conductive plenum is disposed at least partially around the first electrode and wherein the plenum comprises one or more openings which permit the entry of the aqueous fluid while preventing anatomically-specific tissue structures from contacting the first electrode.

11. The method of claim 10 wherein the anatomically-specific tissue comprises targeted tissue.

12. The method of claim 10 wherein the anatomically-specific tissue comprises intact tissue.

13. The method of claim 10 wherein the openings are disposed along a primary axis of the plenum.

14. The method of claim 10 wherein the plenum comprises a shape which is mechanically useful for a surgical procedure.

15. The method of claim 14 wherein the plenum comprises a knife-blade.

16. The method of claim 10 wherein the plenum comprises a textured surface.

17. The method of claim 10 wherein the plenum comprises a roughened surface.

18. The method of claim 10 wherein at least a portion of the plenum extends beyond at least a tip of the first electrode.

19. An electrosurgical tool comprising:
    an at least rigid plenum comprising a non-conductive material disposed at least partially around a first electrode, said plenum comprising a plurality of openings, said openings comprising a size which permits fluid to enter a chamber of said plenum; and
    a second electrode, said first and said second electrodes coaxial with one another.

20. The electrosurgical tool of claim 19 wherein said openings are small enough to inhibit the ability of intact tissue from entering said plenum.

21. The electrosurgical tool of claim 19 wherein said openings are small enough to prevent intact tissue from entering said plenum.

22. The electrosurgical tool of claim 19 wherein an exterior of said plenum comprises a textured surface.

23. The electrosurgical tool of claim 19 wherein said plenum comprises a sharp edge.

24. An electrosurgical tool comprising:
    an at least rigid non-conductive plenum disposed at least partially around a first electrode, said plenum comprising a plurality of openings which permit fluid to enter said plenum, said openings comprising less than about 100% of any side or tip of said plenum; and
    a second electrode, said first and said second electrodes coaxial.

25. The electrosurgical tool of claim 24 wherein said openings comprise less than about 80% of any side or tip of said plenum.

26. The electrosurgical tool of claim 24 wherein said openings comprise less than about 70% of any side or tip of said plenum.

27. The electrosurgical tool of claim 24 wherein said openings comprise less than about 50% of any side or tip of said plenum.

28. The electrosurgical tool of claim 24 wherein said openings comprise less than about 35% of any side or tip of said plenum.

29. The electrosurgical tool of claim 24 wherein said first electrode does not comprise openings.

30. The electrosurgical tool of claim 24 wherein said first electrode does not comprise portals or windows.

31. An electrosurgical tool comprising:
an at least rigid non-conductive plenum disposed at least partially around an electrode, said plenum comprising one or more openings which permit fluid to enter a chamber of said plenum, said plenum not entirely open on a distal tip thereof, said openings arranged only on said distal tip, and wherein an exterior of said plenum comprises a textured surface.

32. The electrosurgical tool of claim 31 wherein said openings are small enough to inhibit the ability of intact tissue from entering said plenum chamber.

33. The electrosurgical tool of claim 31 wherein said openings are small enough to prevent intact tissue from entering said plenum chamber.

34. The electrosurgical tool of claim 31 wherein said plenum comprises a sharpened edge.

35. An electrosurgical tool comprising:
a first electrode surrounded on all sides and ends by an at least rigid plenum surface, said plenum surface comprising one or more openings having a size which permits flow of an aqueous fluid past said electrode; and
a second electrode, said first and second electrodes coaxial with one another.

36. An electrosurgical tool comprising:
an at least rigid non-conductive plenum disposed at least partially around an electrode, said plenum comprising one or more openings which permit fluid to enter a chamber of said plenum, said plenum not entirely open on a distal tip thereof, said openings arranged only on said distal tip, and wherein said plenum comprises a sharpened edge.

37. The electrosurgical tool of claim 36 wherein said openings are small enough to inhibit the ability of intact tissue from entering said plenum chamber.

38. The electrosurgical tool of claim 36 wherein said openings are small enough to prevent intact tissue from entering said plenum chamber.

* * * * *